US005660702A

United States Patent [19]

Starr

[11] Patent Number: 5,660,702
[45] Date of Patent: Aug. 26, 1997

[54] UTILIZATION OF ADDITIVES AND DEFINED STORAGE SYSTEMS TO INCREASE THE STABILITY AND PERFORMANCE OF ELECTROPHORESIS MEDIA

[75] Inventor: Christopher M. Starr, Sonoma, Calif.

[73] Assignee: Glyko, Inc., Novato, Calif.

[21] Appl. No.: 488,313

[22] Filed: Jun. 7, 1995

Related U.S. Application Data

[63] Continuation of Ser. No. 118,957, Sep. 9, 1993.
[51] Int. Cl.⁶ .................. G01N 27/26; G01N 27/447
[52] U.S. Cl. .................. 204/469; 204/456; 204/466; 204/470; 204/606; 204/616
[58] Field of Search .................. 204/299 R, 182.8, 204/180.1

[56] References Cited

U.S. PATENT DOCUMENTS

| | | | |
|---|---|---|---|
| 3,875,045 | 4/1975 | Bergrahm et al. | 204/299 R |
| 4,314,897 | 2/1982 | Monte et al. | 204/182.8 X |
| 4,657,656 | 4/1987 | Ogawa | 204/182.8 X |
| 4,709,810 | 12/1987 | Mayes | 204/182.8 X |
| 4,741,814 | 5/1988 | Mayes et al. | 204/182.8 X |
| 4,759,838 | 7/1988 | Mayes et al. | 204/299 R |
| 4,844,787 | 7/1989 | Akao et al. | 204/182.8 X |
| 4,891,119 | 1/1990 | Ogawa | 204/299 R |
| 5,045,173 | 9/1991 | Guadagno et al. | 204/182.8 X |
| 5,143,643 | 9/1992 | Nochumson et al. | 204/182.8 X |
| 5,275,708 | 1/1994 | Akins, Jr. et al. | 204/182.8 |
| 5,340,461 | 8/1994 | Fukushige et al. | 204/299 R |

FOREIGN PATENT DOCUMENTS

| | | | |
|---|---|---|---|
| 870180 | 5/1971 | Canada | 204/182.8 |
| 225406 | 6/1987 | European Pat. Off. | |
| 9313410 | 7/1993 | WIPO | 204/299 R |

*Primary Examiner*—Kathryn L. Gorgos
*Assistant Examiner*—John S. Starsiak, Jr.
*Attorney, Agent, or Firm*—Pennie & Edmonds LLP

[57] ABSTRACT

The present invention relates to an electrophoresis media comprising a gel and a compound capable of restricting the diffusion of water within the gel. Diffusion restricting compounds useful in the present invention include but are not limited to polyols, polymeric alcohols, polysaccharides, polyoxyethylene ethers, polyamines, polypeptides, gums, zwiterionic detergents and mixtures thereof. The present method relates to any electrophoresis media and includes but is not limited to polyacrylamide, agarose, starch, cellulose acetate and sepharose. A further embodiment of the present invention relates to a stacking gel wherein a diffusion restricting compound is used to prevent diffusion of water between the stack gel and resolving gel. The addition of a diffusion restricting compound to the stacking gel has the particular advantage of causing the stacking gel to become opaque, thereby facilitating the addition of samples to the gel. The present invention also relates to enclosing electrophoresis media within a vacuum sealed container. In yet a further embodiment of the present invention, the media enclosed in the vacuum sealed container further comprises a diffusion restricting compound.

18 Claims, 8 Drawing Sheets

UTILIZATION OF ADDITIVES AND DEFINED STORAGE SYSTEMS TO INCREASE THE STABILITY AND PERFORMANCE OF ELECTROPHORESIS MEDIA

This application is a continuation of co-pending application U.S. Ser. No. 08/118,957, filed Sept. 9, 1993.

FIELD OF THE INVENTION

The present invention relates to the formulation of electrophoresis media. More specifically, the present invention relates to electrophoresis media where diffusion restricting components are added to the electrophoresis media in order to improve both the performance and stability of the electrophoresis media.

BACKGROUND OF THE INVENTION

Electrophoresis is a useful technique for separating molecules including, but not limited to, carbohydrates, proteins, lipids, nucleic acids and derivatives thereof. Electrophoresis operates by separating molecules based on a combination of their molecular charge, their molecular weight and their overall structure.

Separation of molecules by electrophoresis has certain advantages over chromatographic techniques. Electrophoresis media is generally transparent, thereby facilitating visualization of separated molecules. Electrophoresis media is also generally of low flourescence, thereby enabling the use of fluorescent markers. Superior resolution of closely related molecules is achieved as compared to techniques such as Thin Layer Chromatography and High Performance Liquid Chromatography.

In electrophoresis, the molecules are separated as they pass through a media, the media being attached to a current source, such that the anode and cathode are located at opposite ends of the media. By applying a voltage potential difference between the anode and cathode, molecules loaded into the media to be separated migrate toward the electrodes based on their net charge, e.g. molecules with a net negative charge migrate toward the positive electrode or anode. The rate at which the charged molecules migrate is dependent on the charge density of the molecule, referred to as the charge/mass ratio, and the porosity of the electrophoresis media employed. Molecules with a high charge/mass ratio migrate faster toward the oppositely charged electrode than molecules with a low charge/mass ratio. Molecules with the same charge/mass ratio migrate as a discrete band during electrophoresis and are effectively separated from other molecules with different charge/mass ratios.

The rate at which molecules migrate during electrophoresis is also dependent on the restrictive nature of the media. Convection currents generated by uneven heating through the solution often result in significant band distortion and unsatisfactory separations. Consequently many electrophoresis systems utilize a porous electrophoresis media which is designed to minimize molecular diffusion and convection currents during electrophoretic separations.

Many different types of electrophoresis media have been described and used to maximize band resolution and minimize band distortion. Compounds used to formulate electrophoresis media include but are not limited to paper (cellulose), polyacrylamide, agarose, starch, cellulose acetate and sepharose. Compounds used to formulate electrophoresis media are hereinafter referred to as "matrix elements." In general, matrix elements are polymeric in nature and, under the proper conditions, form a porous gel that restricts the movement of molecules through the media during electrophoresis. Electrophoresis media is usually prepared as a porous gel either by the chemical cross-linking of long polymers through the addition of cross-linking reagents, as is the case with polyacrylamide, or by adjusting the component concentration to form a gelatinous network of polymers, as is the case when preparing agarose and starch gels. In either case, the method by which an electrophoresis media is formed from its corresponding matrix element(s) is hereinafter referred to as "curing."

The essential feature of all electrophoresis media is that during electrophoresis, the stable media functions effectively as a molecular sieve so that molecules can be separated based on a combination of their hydrodynamic radii or molecular size and their charge/mass ratio.

In order for the molecular sieving to be effective in separating molecules based on their molecular size, the relationship between the effective pore size of the media and the size of the molecules being separated must be considered. If the media pore size is significantly larger than the size of the molecules being separated, the electrophoretic separation will be based largely on differences in the charge and the effect of molecular sieving will be minimal. Because of their chemical nature, different electrophoresis media possess different nominal pore sizes. As a result, different media have been found to be more appropriate for selected separations. For example, agarose gels have a relatively large pore size and are therefore most effective for separating large molecules such as large nucleic acids. Because of their large pore size, agarose gels are generally not used for protein separations. Effective protein separations require an electrophoresis media having a pore size that closely approximates the protein's smaller molecular size. Electrophoretic protein separations are generally performed using uniform polyacrylamide gels prepared using 10–20% polyacrylamide concentrations. These gels result in a bore size of 100,000–1,000,000 Daltons that effectively separate proteins in the 25,000–200,000 Dalton range.

In order to effectively separate proteins smaller than 25,000 Daltons or small oligonucleotides by electrophoresis, polyacrylamide gels having a concentration greater than 15% are required.

Electrophoresis techniques have also been developed using high percentage (15–40%) polyacrylamide gels for separating carbohydrates through the use of fluorophore labels. Fluorophore assisted carbohydrate electrophoresis permits the electrophoretic separation of a complex mixture of carbohydrates into distinct bands on a gel. Prior to electrophoresis, a carbohydrate mixture for analysis is treated with a fluorophore label that combines with the reducing end of the carbohydrates for analysis. The fluorophore label permits the quantitative measurement of the labeled carbohydrates by fluorescence. The fluorophore label is either itself charged or coupled to a species that imparts a charge on an otherwise uncharged fluorophore. Thus, the fluorophore label not only fluorescently tags the carbohydrates, it also imparts an ionic charge that permits otherwise uncharged carbohydrates to migrate in an electric field. The fluorophore assisted carbohydrate electrophoresis technique is described in detail in U.S. Pat. Nos. 4,317,480, 4,874,492 and in co-pending U.S. patent application Ser. No. 07/317,480, filed Feb. 14, 1989, all of which are incorporated herein by reference. The application of high percent acrylamide gels for separating small proteins, small oligonucleotides and carbohydrates have created a commercial demand for stable high percentage polyacrylamide gels.

Polyacrylamide gels require special preparation. Polyacrylamide gels are usually "poured" as a thin slab within a chamber or space formed between two plates of glass or plastic. This arrangement is called a gel cassette. The thickness of the gel is defined by the distance between the plates of the cassette which in turn is defined by the thickness of the two spacers that extend from the top to the bottom of the cassette along the outside edges. The thickness of the spacers controls the thickness of the electrophoresis media formed within the cassette and is generally between 0.25 mm to 3 mm in thickness. Depending on the application, the resolution of molecular separations generally increases with decreasing media thickness. In addition to the spacers, the cassette also contains a "comb" that is used to form chambers within the media. The number of chambers formed in the media by the comb can range from 1 to as many as 60 or greater, depending on the design of the comb. Prior to electrophoresis, the comb is removed. The samples are then applied into the wells formed by the comb.

In order to obtain optimal separation and resolution of molecules in the sample, polyacrylamide gels are often prepared with regions that contain different effective pore sizes. This is often referred to as a stacking buffer system, also known as "moving boundary electrophoresis." The stacking buffer system is only one example of multiple component electrophoresis media systems.

A stacking buffer system uses techniques known to work with protein and DNA fragments and is described in the book "Gel electrophoresis of proteins: a practical approach," edited by B. D. Hames and D. Rickwood, published by IRL Press.

In a stacking buffer system, a low percent acrylamide solution is layered over a region of high percent acrylamide during the electrophoresis media casting procedure. The lower region of the media that contains the high percentage acrylamide is referred to as the separating gel. The upper region of the media contains the lower percentage acrylamide and is generally referred to as the stacking gel. A distinct interface is generally formed between the separating and stacking gel regions. It is at this interface that a principal called "stacking" occurs during electrophoresis. Stacking enhances the separation and resolution of closely related samples that could not otherwise be achieved without the use of the stacking gel.

Polyacrylamide gels above 15% are extremely difficult to prepare. The polymerization reaction is extremely exothermic wherein the amount of heat generated increases with the percent of acrylamide. The heat generated by the polymerization reaction creates convection currents within the media that results in regions of polymer non-uniformity throughout the media. Bubbles are also formed within the media which further disrupt the media's uniformity and the media's ability to evenly sieve the molecules being separated.

Gradient polyacrylamide gels have been developed to combat these problems. Gradient polyacrylamide gels are gels where the percentage of polyacrylamide increases gradually from 5% at the top of the gel to 27% at the bottom of the gel. The heat generated within the relatively narrow 20-27% polyacrylamide region in the gradient gel can be effectively dissipated using fans or cooling manifolds to cool the cassette during polymerization to produce a satisfactory gel. Proteins in the 10,000-25,000 Dalton range can often be resolved within the narrow 27% polyacrylamide region at the bottom of the gradient gel.

A major problem effecting the stability and resolution of all electrophoresis media is water absorbtion and dissorption. Water absorbtion causes the pores within a given media to increase in size. As noted above, an electrophoresis media's sieving properties are largely governed by the media's pore size. Hence, when the media absorbs water, the media's pore sizes increase thereby enabling molecules to migrate across the media more rapidly. As a result, water absorbtion reduces the resolution achieved by the media since the degree of band separation achieved is reduced when the molecules move more rapidly across the media.

In addition to reducing the resolution (band separation) achieved in each lane of the media, water absorbtion is generally not uniform over the various portions of the media. Rather, water absorbtion in the center region of the electrophoresis media generally occurs at a faster rate than along the edges of the media. As a result, molecules located in the center lanes of the media move across the media at an accelerated rate as compared to the outer lanes. This undermines the reproducibility of the media. The effect water absorbtion has on the media's performance is illustrated in FIG. 1.

Band position comparisons are critical for assigning properties (e.g. molecular weight, net charge, structural characteristics) to a given sample. An effective means for controlling the rate at which water is absorbed by a medium is therefore essential to enhancing the stability and storageability of the media against the effects of water absorbtion.

Water absorbtion is a particularly significant problem in the case of high percentage polyacrylamide gels, "high percentage" referring to gels possessing greater than 20% acrylamide. All polyacrylamide gels absorb water during the polymerization process and during their subsequent storage. The tendency of polyacrylamide gels to absorb water increases with the percentage of acrylamide.

In stack buffer systems, the difference in acrylamide concentration between the stacking gel and the separating gel creates a significant osmotic potential between the two gels that causes water to move from the stacking gel (region of low percent acrylamide) to the separating gel (region of high percent acrylamide). The process of water diffusion from the stacking gel to the separating gel is very rapid and continues until an equilibrium is established between the stacking gel and the separating gel. As a result of water diffusion into the separating gel, current high percentage acrylamide stacking buffer systems are unstable and must be used within a day of their preparation. As a result of their instability, storable high percentage acrylamide gels are not presently commercially available.

When a high percentage acrylamide gel is stored in a buffer, the gel also rapidly absorbs water from the buffer until an equilibrium is established between the buffer and the gel. Unacceptable gels that exhibit a non-uniform pore size result from water diffusion between the high percentage acrylamide gel and air.

There is presently a need to be able to control the diffusion of water within electrophoresis media, between two electrophoresis media having different osmotic potentials, as is the case in multiple component electrophoresis media systems, between electrophoresis media and an accompanying buffer as well as between electrophoresis media and air. Once a method is developed to control the diffusion of water into and between electrophoresis media, the stability and storagability of electrophoresis media will be improved. Further, the reproducibility of the resulting media will be significantly enhanced.

SUMMARY OF THE INVENTION

The present invention relates to an electrophoresis media comprising a gel and a compound capable of restricting the diffusion of water within the gel. Diffusion restricting compounds useful in the present invention include but are not limited to polyols, polymeric alcohols, polysaccharides, polyoxyethylene ethers, polyamines, polypeptides, gums, zwiterionic detergents and mixtures thereof. The present invention relates to any electrophoresis media and includes but is not limited to polyacrylamide, agarose, starch, cellulose acetate and sepharose.

A further embodiment of the present invention relates to a stacking gel wherein a diffusion restricting compound is used to prevent diffusion of water between the stacking gel and resolving gel. The addition of a diffusion restricting compound to the stacking gel has the particular advantage of causing the stacking gel to become colored or opaque, thereby facilitating the addition of samples to the gel.

The present invention also relates to enclosing electrophoresis media in a vacuum sealed container. In yet a further embodiment of the present invention, the media enclosed within the vacuum sealed container further comprises a diffusion restricting compound. In a further embodiment of the present invention, the media is enclosed in the vacuum sealed container using inert gases.

BRIEF DESCRIPTION OF THE FIGURES

The invention will be better understood by reference to the appended Figures, of which.

DETAILED DESCRIPTION OF THE INVENTION

Figure 1:
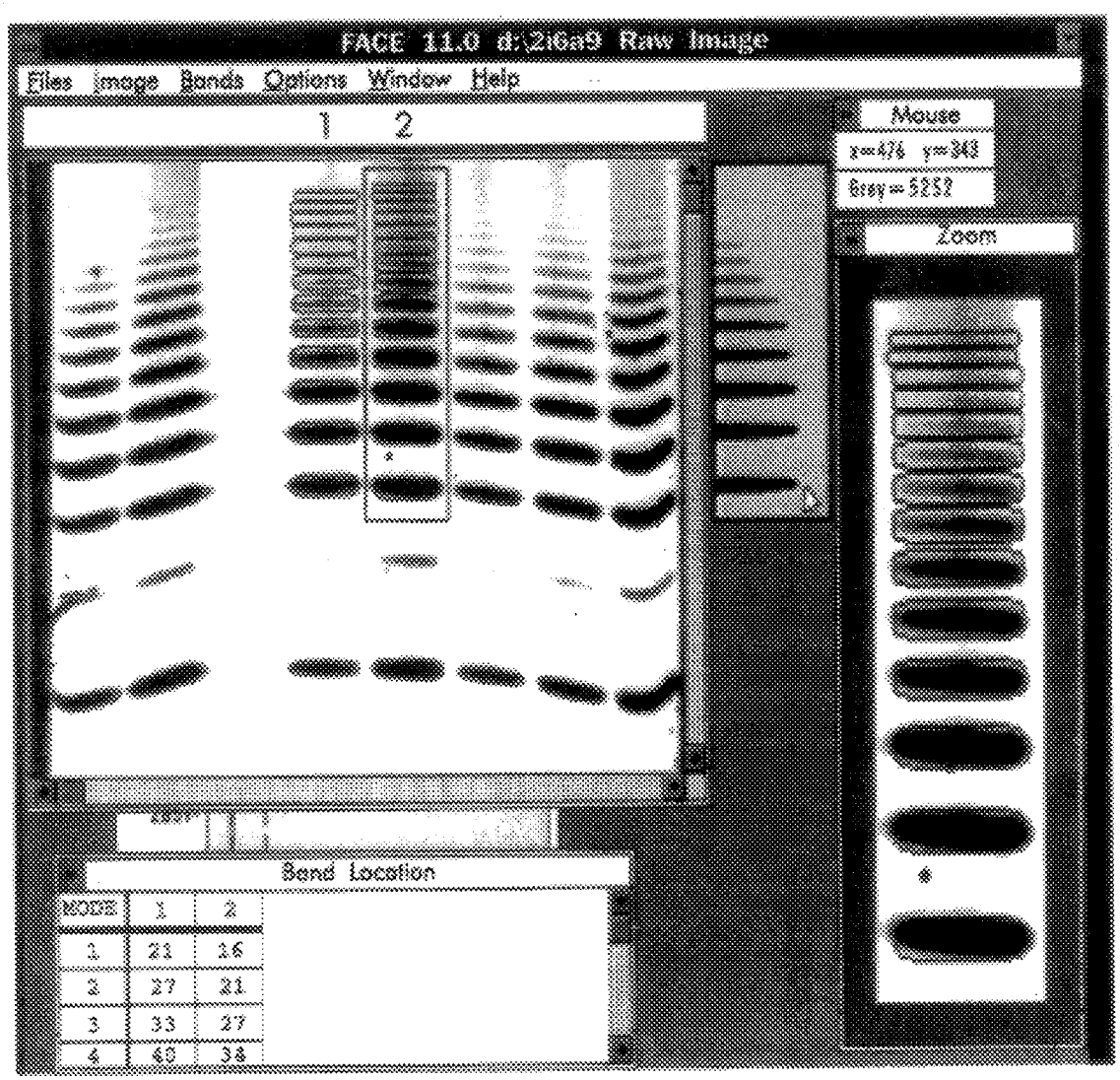
FIG. 1 depicts the separation and resolution of a partial wheat starch digest using a 21% polyacrylamide stacking electrophoresis gel containing no polyethylene glycol that had been stored at 4° C. for 29 days. The gel depicted in FIG. 1 was prepared according to Example 1.

The present invention relates to a method for restricting the diffusion of water into and within electrophoresis media by the addition of certain diffusion restricting compounds to the electrophoresis media. By restricting the diffusion of water into and within electrophoresis media, the stability, shelf life and reproducibility of the electrophoresis media is enhanced. Since the rate of water diffusion is temperature dependent, reduction of the rate of diffusion of water into and between the media also enhances the thermal stability of the media.

The present invention also relates to electrophoresis media having improved stability, shelf life and reproducibility as a result of the addition of a diffusion restricting compound to the media.

Water diffusion restriction is achieved by the addition of certain diffusion restricting compounds that immobilize water by their own hydration, thereby preventing water from diffusing into and within electrophoresis media. The diffusion restricting compounds of the present invention are hydrophilic uncharge molecules and include polyols, polymeric alcohols, polysaccharides, polyoxyethylene ethers, polyamines, polypeptides, gums, zwiterionic detergents and mixtures thereof. It is understood that mixtures of different diffusion restricting compounds may be employed in the present invention. Polyols and polymeric alcohols useful in the present invention include but are not limited to polyethylene glycol homopolymers, polypropylene glycol homopolymers, copolymers of ethylene glycol with propylene glycol, wherein said homopolymers and copolymers are unsubstituted or substituted at one end with an alkyl group, polyoxyethylated polyols, polyvinyl alcohol, polyethylene oxide and polypropylene oxide. Gums useful in the present invention also include but are not limited to guar gum, locust bean gum, gum tragacanth, and xanthan gum. Polysaccharides useful in the present invention include but are not limited to dextrans, n-Decyl-beta-D-glucopyranoside, digitonin, n-dodecyl-beta-D-glucopyranoside, n-heptyl-beta-D-glucopyranoside, n-octyl-beta-D-glucopyranoside, n-octyl-alpha-D-glucopyranoside, n-nonyl-beta-D-glucopyranoside, DIGITONIN, NONIDET P-40 and TRITON X-100. Zwiterionic detergents useful in the present invention include CHAPS and CHAPSO. Polyethylene glycol is the most preferred hydrophilic, uncharged diffusion restricting compound for use with high concentration acrylamide stacking buffer systems.

The diffusion restricting compounds are added to the portion of the electrophoresis media or media system within which one wants to immobilize water. For example, in order to prevent the diffusion of water within a media, the diffusion restricting compound is added to the media itself. If a storage buffer is used in conjunction with an electrophoresis media, a diffusion restricting compound may be added to the storage buffer in order to prevent diffusion of water from the storage buffer into the media. In a stack buffer system, the diffusion restricting compound is added to the stacking gel in order to prevent the water within the stacking gel from being drawn into the separating gel.

The diffusion restricting compounds may be introduced into the media during curing either as a solution or in solid form. Additional means for adding the diffusion restricting compound can be determined by one of ordinary skill in the art. In general, the addition of diffusion restricting compounds do not effect the curing of electrophoresis media. Therefore, electrophoresis media incorporating a diffusion restricting compound can be made according to methods known in the art.

Even distribution of the diffusion restricting compounds within the media is important in order to maintain even water diffusion control. Therefore, it is preferred that the diffusion restricting compounds be added before the media is cured. If it is desired to prevent the diffusion of water from a buffer into a gel, the diffusion restricting compound may be added directly to the buffer.

Through the addition of these diffusion restricting compounds, diffusion of water into and within the media is prevented thereby enabling uniform pore size to be maintained.

The concentration of a particular diffusion restricting compound needed to control diffusion depends greatly on the molecular weight of the compound since the molecular weight of the compound directly impacts the resulting molarity of the compound within the gel.

Without being bound by theory, the diffusion restricting compounds used in the present invention serve to counteract osmotic potential imbalances within the electrophoresis media or between two contacting media having different osmotic potentials, as is present between the components of a stack buffering system or between an electrophoresis media and a buffer. The extent to which the diffusion restricting compound is able to counteract the osmotic potential imbalance depends on the hydrophilicity of the compound and its molar concentration since these factors influence the number of water molecules that hydrate the diffusion restricting compound. The concentration of any particular diffusion restricting compound needed to counteract the osmotic imbalance will also depend on the magnitude of the osmotical potential to be overcome. A lower concentration of diffusion restricting compound is need to counteract the osmotic imbalance within a uniform gel than is needed to counteract the osmotic imbalance present between a stacking gel and a separating gel in a stacking buffer system. A simple and rapid method for determining the optimal amount of any particular diffusion restricting compound to add to an electrophoresis media or to an accompanying buffer is provided in Example 5. As can be seen by Example 5, the optimal concentration of compound to add can be rapidly and efficiently determined.

In addition to restricting the diffusion of water within the gel, diffusion restricting compounds cause the portion of the gel in which they are added to become colored or opaque, thereby greatly facilitating the addition of samples to the gel. In the case of transparent media, sample wells are not readily apparent and are thus often difficult to locate. By contrast, sample wells are readily apparent when the gel is either colored or opaque, thereby facilitating the addition of samples into the wells.

The present invention also provides for kits for performing electrophoresis comprising a gel and a compound capable of restricting the diffusion of water within the gel. Kits may also include but are not limited to various combinations of the following items: fluorophores, fluorophore-labelled assay substrates, reagents for electrophoresis assays, electrophoresis standards (including carbohydrate-modifying enzyme standards and modified assay substrates standards, i.e., substrates both before and after structural alterations by the carbohydrate-modifying enzyme of interest), antibodies, CCDs, computer software for analysis of results, gel fluorescence illumination equipment, chromogenic indicators, photographic equipment, reagent containers, cartridges containing carbohydrate-modifying enzymes immobilized on reaction matrix gels, carbohydrate substrates for use in synthesis, apparatus for performing methods of carbohydrate synthesis, apparatus for performing the subject assays for carbohydrates, and apparatus for performing the subject assays for the detection of carbohydrate-modifying enzymes. Compounds included in kits are preferably provided in pre-measured portions and pre-mixed solutions so as to provide for reproducibility and minimize error in performing particular syntheses and/or assays. Kits also preferably contain instructions. Instructions are directed to various steps in performing the subject assays and/or syntheses for which the kits are designed.

A further embodiment of the present invention relates to the storage of gels in a vacuum sealed container as a means for enhancing the stability of the gels over long periods of time by further preventing the diffusion of water into and within a gel. It has been found that the diffusion of water into and within a gel can be further limited by sealing and storing the gel in a vacuum sealed container until the gel is to be used. By storing gels in vacuum sealed containers, the gels may be stored in the absence of buffers or air, thereby minimizing the movement of water within the gel. As a result of this storage method, the initial pore size of the gel and hence the separation capacity of the gel is maintained, even after prolonged storage.

Inert gases are preferably used to vacuum seal the gels within the containers. Inert gases that may be used include but are not limited to noble gases such as argon and xenon and other chemically unreactive gases such as nitrogen.

The present invention also relates to the use of a vacuum sealed container within which the electrophoresis media is stored. It has been observed that water diffusion within and into electrophoresis media can be reduced by storing gels in a vacuum sealed container. It should be noted that the stability and storage advantages derived by storing gels in a vacuum sealed container are independent of the use of a diffusion restricting compound. However, it is preferred that the electrophoresis media be treated with a diffusion restricting compound and stored in a vacuum sealed container.

The present invention is illustrated by the following examples. Further objectives and advantages other than those set forth above will become apparent from the examples and accompanying drawings.

EXAMPLES

Example 1

Preparation of 5% Polyacrylamide Gel Containing No Added Diffusion Restricting Compound Polyacrylamide electrophoresis stacking gels designed to separate oligosaccharides containing 21% polyacrylamide with no diffusion restricting compound were prepared in a 0.5 mm glass cassette as follows.

The separating gel was prepared by adding 52 ml of a 60% acrylamide: 1.6% bisacrylamide solution to 60 ml of Milli-Q water, and 37.5 ml of 448 mm Tris-acetate pH 7.0. The solution was mixed and degassed for 3 minutes. To the solution was added 50 ul TEMED and 0.5 ml of 10% Ammonium persulfate. The mixture as immediately poured into a 0.5 mm glass cassette essentially as described by U. Laemmli (Nature 1970) and the gel was overlayed with water. The stacking gel was prepared by adding 6.6 ml of a 60% acrylamide: 1.6% bis-acrylamide solution to 25.4 ml of Milli-Q water, 12.4 ml of 448 mm Tris-acetate pH 7.0 and 5.3 ml of water, the 5.3 ml replacing the 50% w/v solution of polyethylene glycol, MW 8,000 in water that was added in Examples 3 and 4. The mixture was degassed for 2 minutes and 100 ul of TEMED and 250 ul of 10% ammonium persulfate was added. The water overlay was removed from the polymerized separating gel an eight well comb was positioned between the glass plates of the cassette and the stacking solution was poured into the region around the comb. The stack was allowed to polymerize for 30 minutes during which time the stack remains clear and colorless.

Example 2

Preparation of 21% Polyacrylamide Gel Containing 5% Polyethylene Glycol

Polyacrylamide electrophoresis stacking gels designed to separate oligosaccharides containing 21% polyacrylamide and 5% polyethylene glycol were prepared in a 0.5 mm glass cassette as follows.

The separating gel was prepared by adding 52 ml of a 60% acrylamide: 1.6% bisacrylamide solution to 60 ml of Milli-Q water, and 37.5 ml of 448 mm Trisacetate pH 7.0. The solution was mixed and degassed for 3 minutes. To the solution was added 50 ul TEMED and 0.5 ml of 10% Ammonium persulfate. The mixture as immediately poured into a 0.5 mm glass cassette essentially as described by U. Laemmli (Nature 1970) and the gel was overlayed with water. The stacking gel was prepared by adding 6.6 ml of a 60% acrylamide: 1.6% bis-acrylamide solution to 25.4 ml of Milli-Q water, 12.4 ml of 448 mm Tris-acetate pH 7.0 and 5.3 ml of a 50% w/v solution of polyethylene glycol, MW 8,000 in water. The mixture was degassed for 2 minutes and 100 ul of TEMED and 250 ul of 10% ammonium persulfate was added. The water overlay was removed from the polymerized separating gel an eight well comb was positioned between the glass plates of the cassette and the stacking solution was poured into the region around the comb. The stack was allowed to polymerize for 30 minutes during which time the stack became white in color and opaque.

Example 3

Preparation of 20% Polyacrylamide Gel Containing 5% Polyethylene Glycol

Polyacrylamide electrophoresis staccking gels designed to separate monosaccharides containing 20% polyacrylamide and 5% polyethylene glycol were prepared in a 0.5 mm glass cassette as follows.

The separating gel was prepared by adding 67 ml of a 60% acrylamide: 1.6% bisacrylamide solution to 72 ml of Milli-Q water, 40 ml of 25% glycerol (v/v in water) and 20 ml of 448 mm Tris-acetate pH 7.0. The solution was mixed and degassed for 3 minutes. To the solution was added 50 ul TEMED and 0.5 ml of 10% Ammonium persulfate. The mixture as immediately poured into a 0.5 mm glass cassette essentially as described by U. Laemmli.(Nature 1970) and the gel was overlayed with water. The stacking gel was prepared by adding 8 ml of a 60% acrylamide:1.6% bis-acrylamide solution to 28.7 ml of Milli-Q water, 6 ml of 448 mm Tris-acetate pH 7.0, 12 ml of 25% glycerol (v/v in water) and 5.3 ml of a 50% w/v solution of polyethylene glycol, 8,000 in water. The mixture was degassed for 2 minutes and 100 ul of TEMED and 250 ul of 10% ammonium persulfate was added. The water overlay was removed from the polymerized separating gel an eight well comb was positioned between the glass plates of the cassette and the stacking solution was poured into the region around the comb. The stack was allowed to polymerize for 30 minutes during which time the stack became white in color and opaque.

Example 4

Comparison of Stability of Gels with and without Hydrophilic, Uncharged Additive The stability of the gels produced in Examples 1–3 were accessed by electrophoresis of fluorophore-labeled carbohydrates prepared as described in U.S. Pat. Nos. 4,317,480 and 4,874,492 for the separation of fluorophore-labeled oligosaccharides on high percent (20–40%) polyacrylamide gels.

A gel prepared according to Example 1 was stored at 4° C. for 29 days, loaded with a solution of wheat starch that had been partially digested with α-amylase which was then electrophoretically separated. FIG. 1 depicts the results of running the gel from Example 1 after it had been stored for 29 days at 4° C.

Figure 2:
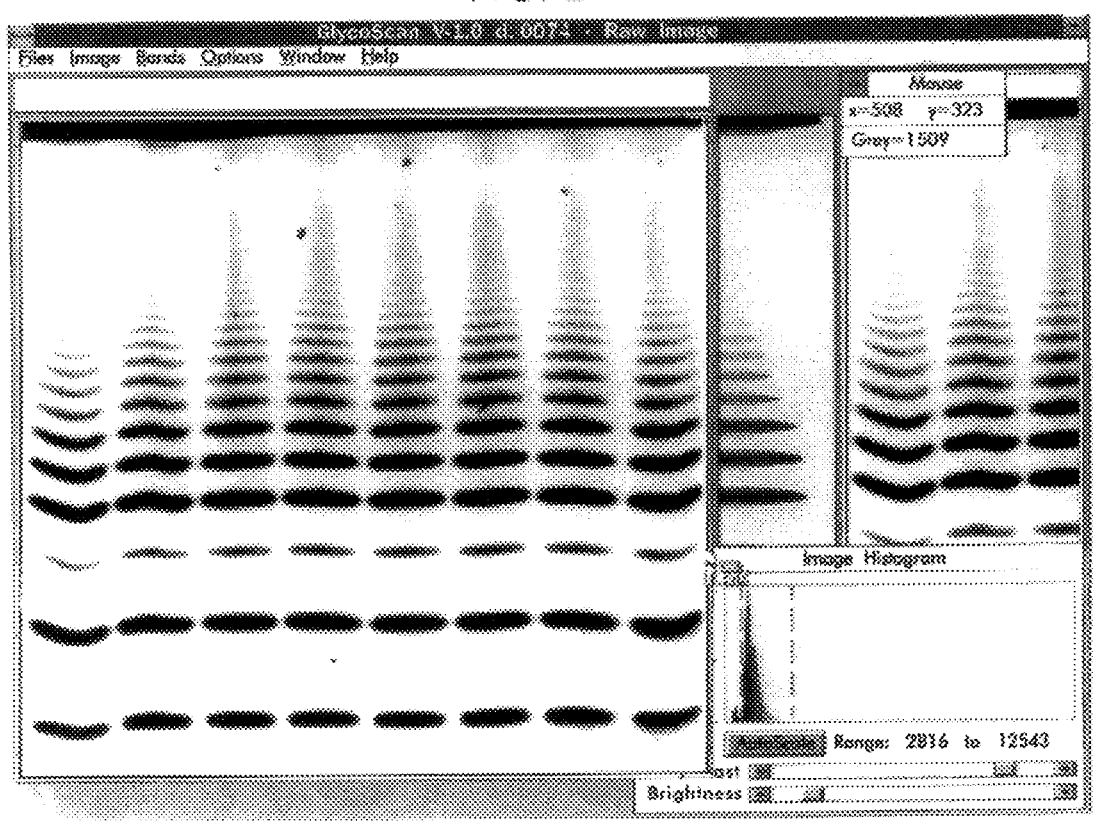
FIG. 2 depicts the separation and resolution of a partial wheat starch digest using a 21% polyacrylamide stacking electrophoresis gel containing 5% polyethylene glycol that had been stored at 22°–25 ° C. for 35 days. The gel depicted in FIG. 2 was prepared according to Example 2.

A gel prepared according to Example 2 was stored at room temperature for 35 days, loaded with a solution of wheat starch that had been partially digested with α-amylase. FIG. 2 depicts the results of running the gel from Example 2 after it had been stored for 35 days at room temperature.

As can be seen in FIG. 1, when no diffusion restricting compound is added, molecules in different lanes of the gel migrate across the gel at differing rates. However, as can be seen in FIG. 2, when a diffusion restricting compound is added, molecules in different lanes of the gel migrate across the gel at equivalent rates. These results clearly demonstrate that the addition of a diffusion restricting compound, such as polyethylene glycol, substantially enhances the stability of the gel.

It should be further highlighted that the gel containing a diffusion restricting compound prepared according to Example 2 was stored at room temperature while the gel prepared according to Example 1 which does not contain a diffusion restricting compound was stored at 4° C. The gel prepared according to Example 1 was refrigerated in order to slow the decomposition of the gel. It has generally been observed that refrigeration at 4° C. slows the decomposition rate of a gel four fold relative to the decomposition rate at 22° C. Hence, the addition a diffusion restricting compound to the gel has been shown to very significantly increased the gel's stability.

Figure 3:
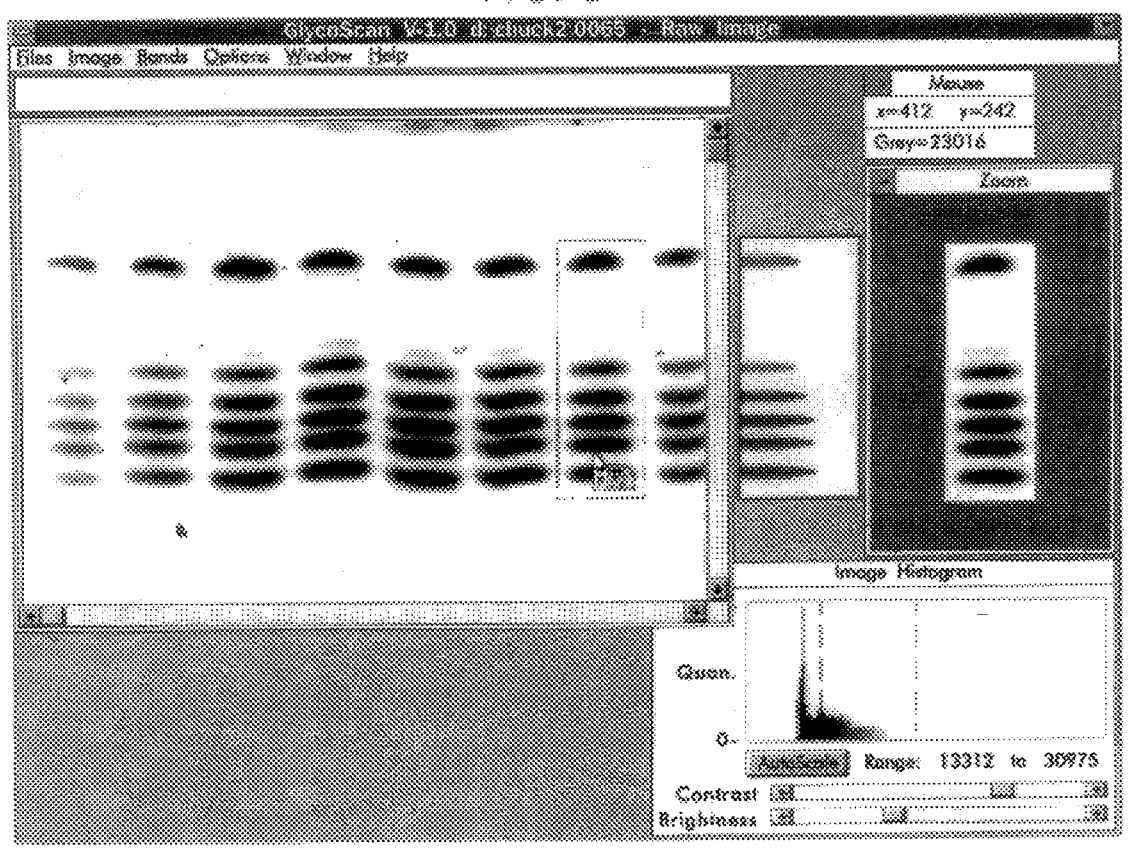
FIG. 3 depicts the separation and resolution of a solution of seven monosaccharides using a 20% polyacrylamide stacking electrophoresis gel containing 5% polyethylene glycol that had been stored at 22°–25° C. for 76 days.

A gel prepared according to Example 3 was stored at room temperature for 76 days. Afterward, the gel was loaded with an equimolar solution of seven fluorescently labelled monosaccharides which were then electrophoretically separated. As can be seen in FIG. 3, the migration rate of the monosaccharides did not vary lane to lane. Thus, as can be seen with regard to FIG. 3, the addition of a diffusion restricting compound such as polyethylene glycol substantially enhances the stability of the gel.

Example 5

Method for Determining Optimal Concentration of Additive to Introduce

The following example exemplifies how one of ordinary skill determines the preferred diffusion restricting compound and matrix element concentrations.

In the present example, gels containing 4% acrylamide and either 2%, 5% and 10% polyethylene glycol were prepared according to Example 1. The gels were then stored at 37° C. for 5 days. The gels were stored above room temperature in order to accelerate the aging process. It has been observed that storage of a gel at 37° C. causes the gel to age eight times faster than if stored at room temperature.

Figure 4:
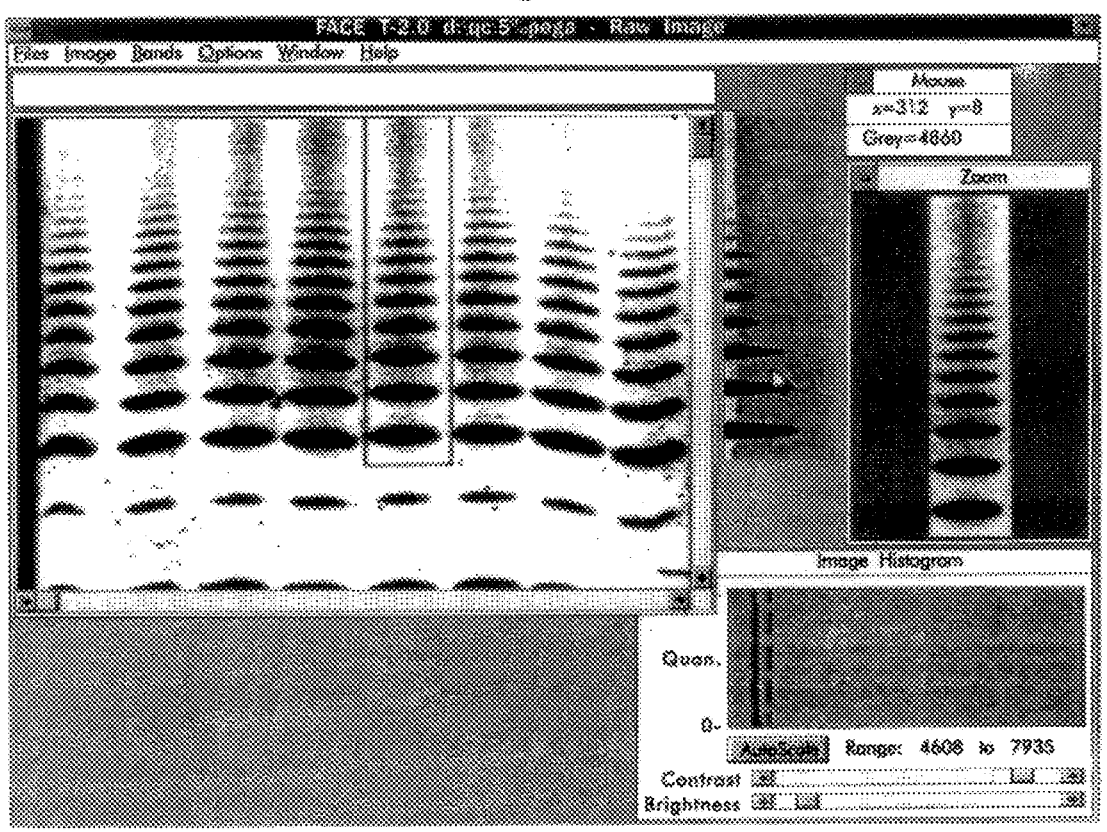
FIG. 4 depicts the separation and resolution of a partial wheat starch digest using a polyacrylamide stacking electrophoresis gel containing 4% acrylamide and 5% polyethylene glycol that had been stored at 37° C. for 5 days.
Figure 5:
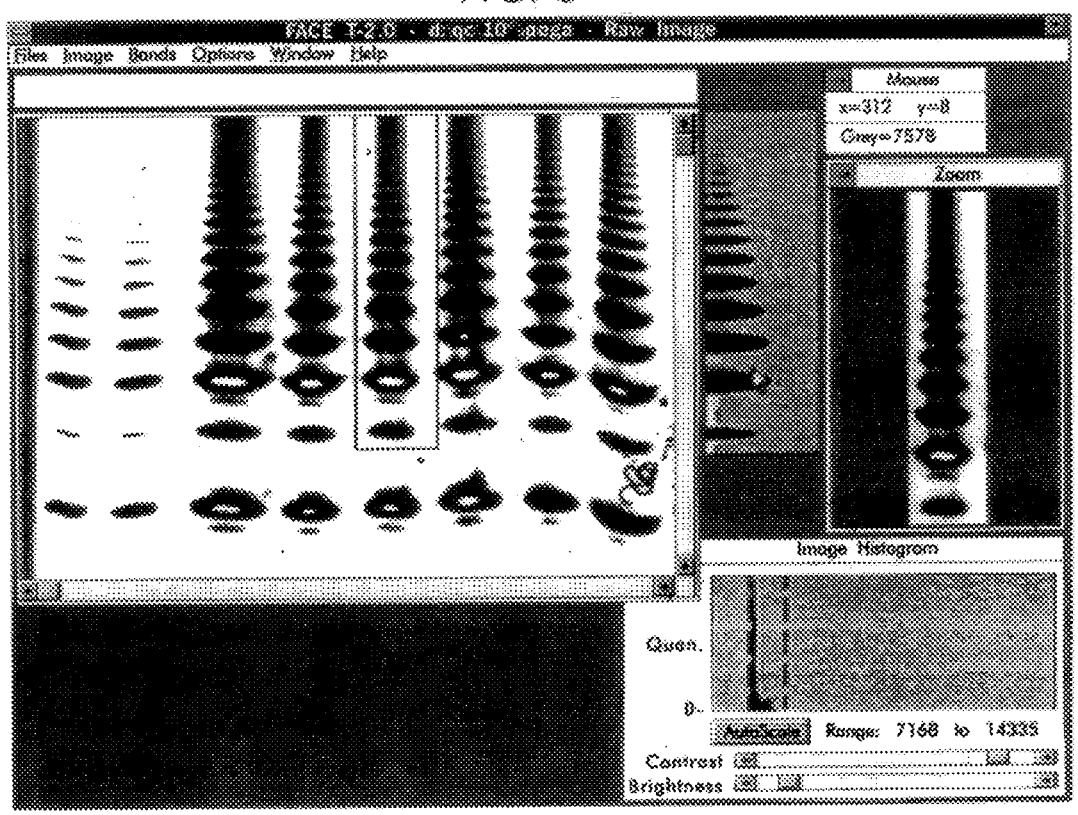
FIG. 5 depicts the separation and resolution of a partial wheat starch digest using a polyacrylamide stacking electrophoresis gel containing 4% acrylamide and 10% polyethylene glycol that had been stored at 37° C. for 5 days.

After five days, the gels containing 2% polyethylene glycol were not usable because the stacking portion of the gels had become dried out, the water within the stacking portion having diffused to the adjacent separating gel. Gels containing 5% and 10% polyethylene glycol were loaded with a solution of wheat starch that had been partially digested with α-amylase, run and compared. These gels are depicted in FIGS. 4 and 5 respectively. As can be seen from FIGS. 4 and 5, the addition of 5% polyethylene glycol provided more focused, better resolved bands. Based on these results, 5% polyethylene glycol was determined to be the preferred additive concentration.

Figure 6:
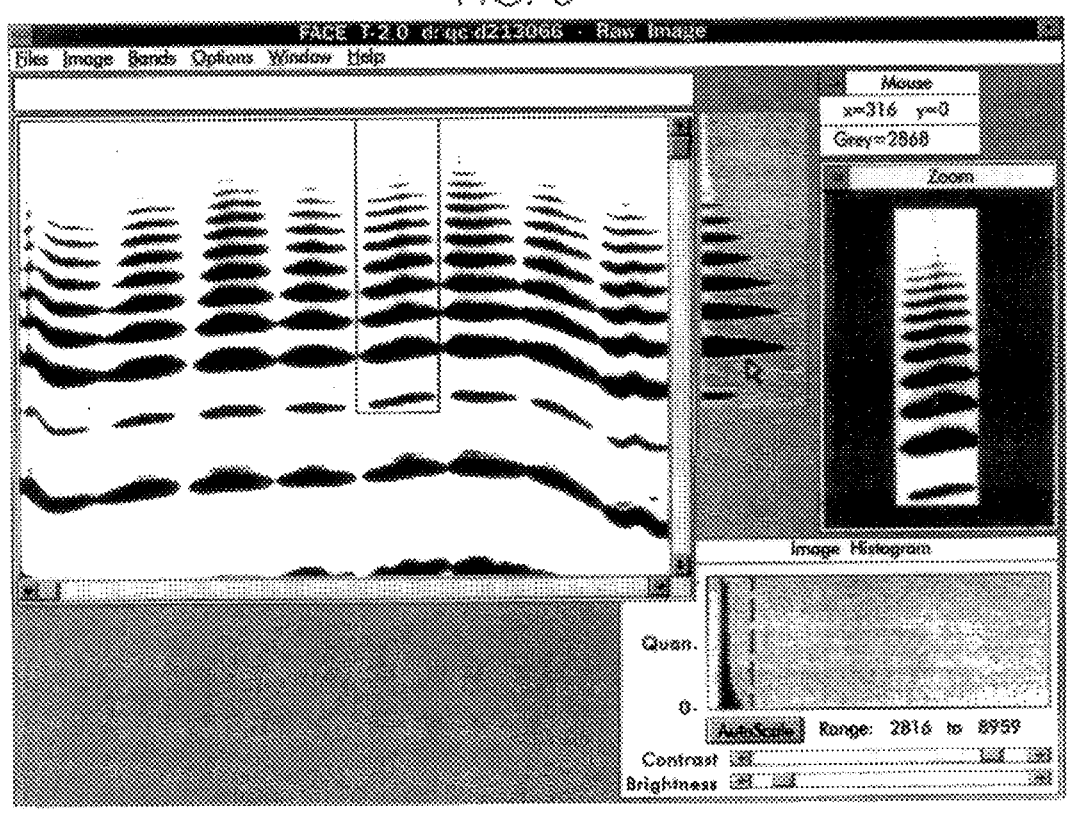
FIG. 6 depicts the separation and resolution of a partial wheat starch digest using a polyacrylamide stacking electrophoresis gel containing 6% acrylamide and 5% polyethylene glycol that had been stored at 37° C. for 5 days.
Figure 7:
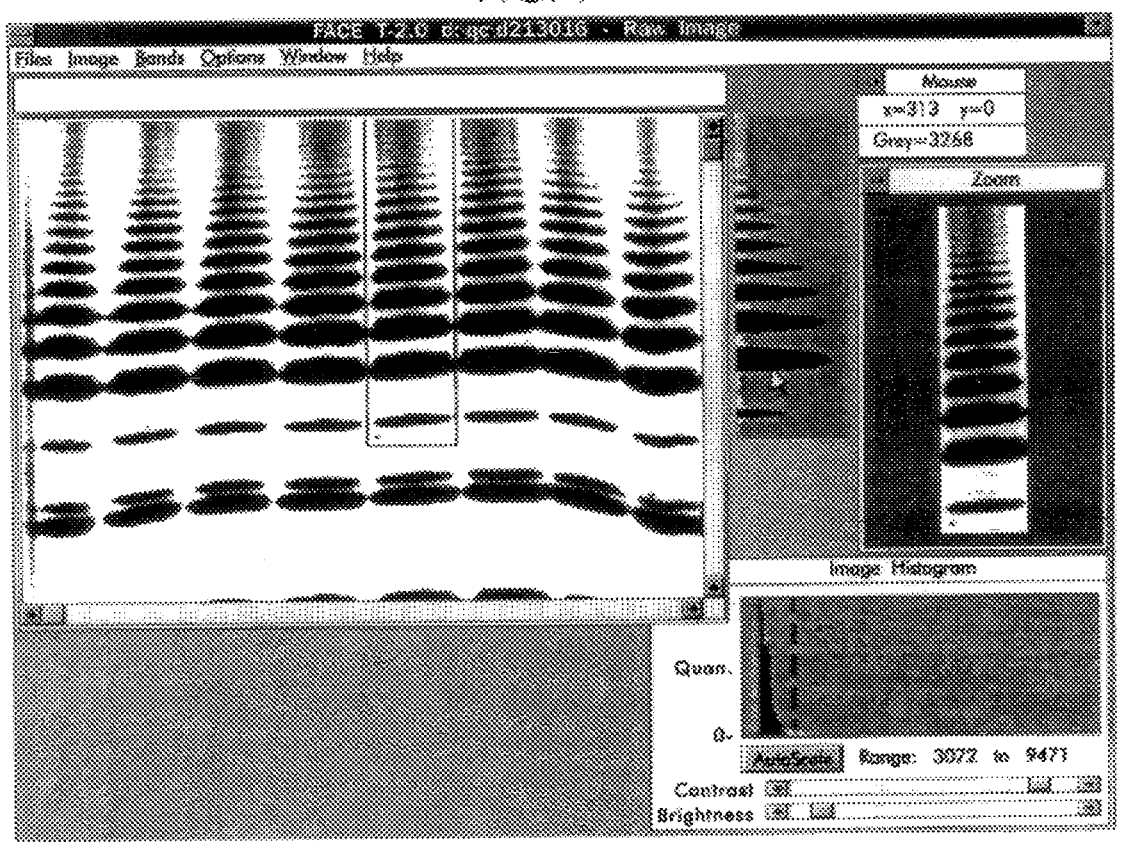
FIG. 7 depicts the separation and resolution of a partial wheat starch digest using a polyacrylamide stacking electrophoresis gel containing 8% acrylamide and 5% polyethylene glycol that had been stored at 37° C. for 5 days.
Figure 8:
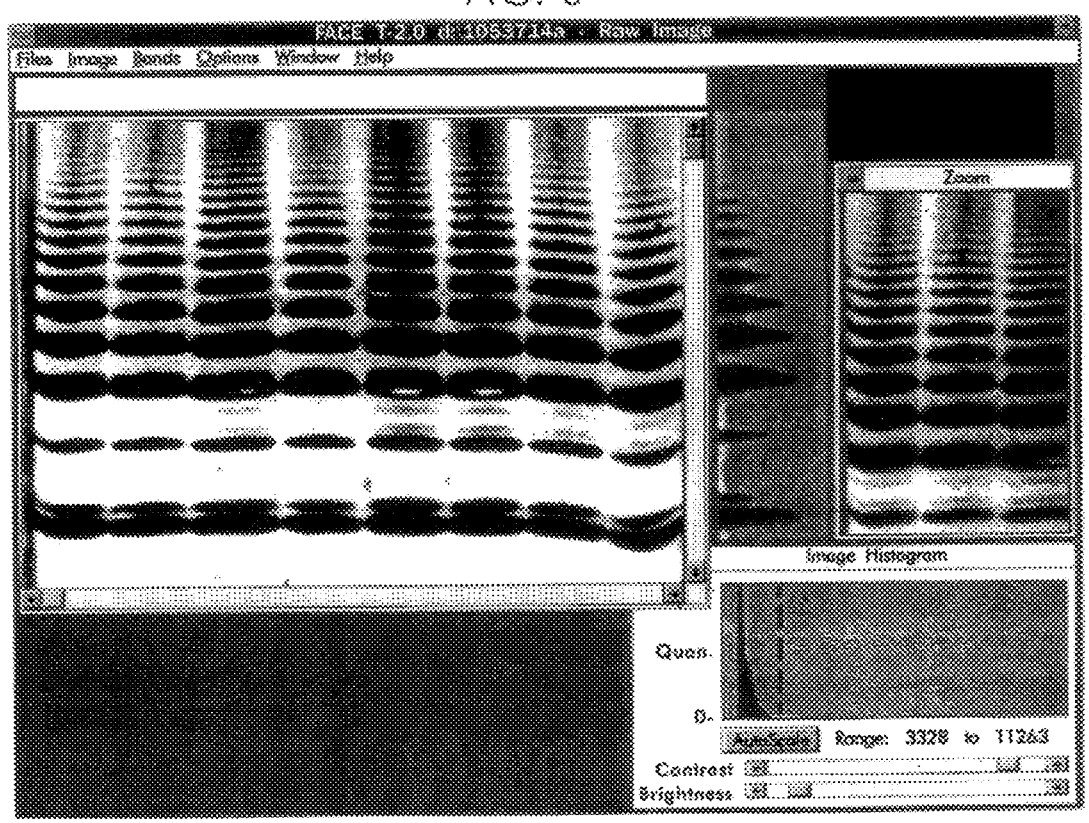
FIG. 8 depicts the separation and resolution of a partial wheat starch digest using a polyacrylamide stacking electrophoresis gel containing 10% acrylamide and 5% polyethylene glycol that had been stored at 37° C. for 5 days.

In order to determine the preferred acrylamide concentration, gels were prepared according to Example 1 that contained 5% polyethylene glycol and either 6%, 8% or 10% acrylamide. Each gel was then loaded with a solution of wheat starch that had been partially digested with α-amylase, run and compared. These gels are depicted in FIGS. 6, 7 and 8 respectively. As can be seen from FIGS. 6, 7 and 8, superior gel stability and band resolution was achieved using 10% acrylamide. Based on this analysis, it was determined that a gel prepared according to Example 1 comprising 5% polyethylene glycol and 10% acrylamide constituted one of the preferred embodiments of the present invention.

While this example relates to the determination of the preferred embodiment with regard to polyethylene glycol and acrylamide, it is understood that the same analysis may be conducted with regard to other diffusion restricting compounds and other matrix elements by those of ordinary skill in the art.

While the invention of this patent application is disclosed by reference to the aforementioned examples, it is to be understood that these examples are intended in an illustrative rather than limiting sense, as it is contemplated that modifications will readily occur to those skilled in the art, within the spirit of the invention and the scope of the appended claims.

What is claimed is:

1. An electrophoresis media comprising
   a gel selected from the group consisting of polyacrylamide, starch, cellulose acetate and sepharose; and
   a diffusion restricting compound selected from the group consisting of polyols, polymeric alcohols, polysaccharides, polyoxethylene ethers, polyamines, polypeptides, gums, zwiterionic detergents and mixtures thereof,
   wherein the diffusion restricting compound causes the media to become colored or opaque.

2. An electrophoresis gel cassette comprising a gel-holder, and a multi-component electrophoresis media comprising:
   a first gel; and
   a second gel, the second gel being in contact with the first gel;
   wherein the first and second gel are comprised of a common matrix element, selected from the group consisting of polyacrylamide, starch, cellulose acetate and sepharose, wherein said common matrix element is present in the second gel in a higher concentration than the first gel; and
   wherein the first gel further comprises a diffusion restricting compound.

3. The electrophoresis gel cassette of claim 2 wherein said gel-holder is useful with electrophoresis apparatus selected from the group consisting of capillary gel electrophoresis, tube gel electrophoresis, and slab gel electrophoresis.

4. A method for improving the storage properties of an electrophoresis media comprising the step of vacuum sealing the electrophoresis media in a container.

5. The method of claim 4 wherein the electrophoresis media contains a diffusion restricting compound.

6. The method of claim 5 wherein the diffusion restricting compound is selected from the group consisting of polyols, polymeric alcohols, polysaccharides, polyoxyethylene ethers, polyamines, polypeptides, gums, zwiterionic detergents and mixtures thereof.

7. The method of claim 6 wherein the diffusion restricting compound is polyethylene glycol.

8. The method of claim 4 wherein the electrophoresis media is vacuum sealed within the container using inert gases.

9. A kit for performing electrophoresis comprising a multi-component electrophoresis media wherein the electrophoresis media comprises:
   a first gel; and
   a second gel, the second gel being in contact with the first gel;
   wherein the first and second gel are comprised of a common matrix element selected from the group consisting of polyacrylamide, starch, cellulose acetate and sepharose, wherein said common matrix element is present in the second gel in a higher concentration than the first gel; and
   wherein the first gel further comprises a diffusion restricting compound.

10. A kit according to claim 9 wherein the diffusion restricting compound is selected from the group consisting of polyols, polymeric alcohols, polysaccharides, polyoxyethylene ethers, polyamines, polypeptides, gums, zwiterionic detergents and mixtures thereof.

11. A kit according to claim 10 wherein the diffusion restricting compound is polyethylene glycol.

12. A kit according to claim 9 wherein the matrix element is polyacrylamide.

13. A gel storage packet comprising: an electrophoresis media and a container, wherein the electrophoresis media is vacuum sealed within the container.

14. A gel packet according to claim 13 wherein the electrophoresis media further comprises a diffusion restricting compound.

15. A gel packet according to claim 14 wherein the diffusion restricting compound is selected from the group consisting of polyols, polymeric alcohols, polysaccharides, polyoxyethylene ethers, polyamines, polypeptides, gums, zwiterionic detergents and mixtures thereof.

16. A gel packet according to claim 15 wherein the diffusion restricting compound is polyethylene glycol.

17. A gel packet according to claim 13 wherein the electrophoresis media is a multi-component electrophoresis media comprising:
   a first gel; and
   a second gel, the second gel being in contact with the first gel;
   wherein the first and second gel are comprised of a common matrix element, that common matrix element being present in the second gel in a higher concentration than the first gel; and
   wherein the first gel further comprises a diffusion restricting compound.

18. A gel packet according to claim 13 wherein the electrophoresis media is vacuum sealed within the container using inert gases.

* * * * *